United States Patent [19]

Takagi et al.

[11] 4,454,329

[45] Jun. 12, 1984

[54] PROCESS FOR PREPARATION OF TOCOPHEROL CONCENTRATES

[75] Inventors: Yoshiaki Takagi; Yoshinori Kai, both of Kanagawa, Japan

[73] Assignee: The Nisshin Oil Mills, Ltd., Tokyo, Japan

[21] Appl. No.: 279,650

[22] Filed: Jul. 2, 1981

[30] Foreign Application Priority Data

Jul. 4, 1980 [JP] Japan .................................. 55-90676
Mar. 17, 1981 [JP] Japan .................................. 56-37310

[51] Int. Cl.$^3$ .......................................... C07D 311/72
[52] U.S. Cl. .................................................. 549/413
[58] Field of Search ...................... 260/345.6; 549/413

[56] References Cited

U.S. PATENT DOCUMENTS 2,317,353  4/1943  Baxter .
2,349,271  5/1944  Baxter ............................... 260/345.6
2,349,789  5/1944  Hickman ........................... 260/345.6

Primary Examiner—Nicky Chan
Attorney, Agent, or Firm—Sughrue, Mion, Zinn, Macpeak & Seas

[57] ABSTRACT

A tocopherol concentrate having a high tocopherol concentration can be obtained in a high yield by subjecting a deodorized distillate formed as a by-product at the step of deodorizing oils and fats to esterification of free fatty acids by addition of an alcohol or removal of free fatty acids by distillation and then to hydrogenation. A tocopherol concentrate can also be obtained by subjecting a deodorized distillate to esterification by addition of a polyhydric alcohol and then to distillation. Concentrates having a high concentration and a high quality can be obtained in a high yield with a good operation efficiency.

2 Claims, No Drawings

PROCESS FOR PREPARATION OF TOCOPHEROL CONCENTRATES

BACKGROUND OF THE INVENTION (1) Field of the Invention

The present invention relates to a process for preparing a tocopherol concentrate from a deodorized distillate formed as a by-product at the step of deodorizing oils and fats.

(2) Description of the Prior Art $\alpha$-, $\beta$-, $\gamma$- and $\delta$-Tocopherols (hereinafter referred to as "tocopherols") are ordinarily contained in an amount of about 1 to about 20% by weight in a deodorized scum, deodorized sludge or hot well oil dreg (hereinafter referred to as "deodorized distillate") formed as a by-product at the step of deodorizing oils and fats such as soybean oil, linseed oil, cotton seed oil, safflower oil, rice bran oil, corn oil and sunflower oil. Accordingly, the deodorized distillate is valuable as the material for production of vitamin E or an antioxidant. However, this deodorized distillate contains 30 to 60% by weight of free fatty acids, 10 to 35% by weight of sterols and esters thereof, 10 to 30% by weight of hydrocarbons, 10 to 20% by weight of glycerides and several % by weight of other substances in addition to tocopherols. Accordingly, in order to obtain a tocopherol concentrate from such deodorized distillate, it is important to remove these substances, especially free fatty acids.

Various processes have heretofore been proposed for obtaining tocopherol concentrates from deodorized distillates. For example, Japanese Patent Publication No. 23147/70 discloses a process for the preparation of tocopherol concentrates which comprises subjecting a deodorized distillate to a halogenohydrogenation treatment for separating and removing sterols and then to distillation. However, since a hydrogen halide is used in this process, the operation is not preferred, and furthermore, since removal of free fatty acids is not intended, the concentration of tocopherols in the obtained concentrate is low and no satisfactory product is obtained.

As another known process, there can be mentioned an ester exchange process comprising ester-exchanging a deodorized distillate with methanol, subjecting the ester exchange product to distillation to remove free fatty acids in the form of methyl esters and concentrating the residue by molecular distillation or the like. In this process, since the deodorized distillate and methanol are heated and refluxed with a strong acid catalyst such as hydrochloric acid or sulfuric acid for a long time, by-products are readily formed, and the viscosity of the residue left after removal of methyl esters of fatty acids by distillation is high and therefore, the operation efficiency is reduced at the subsequent step of concentration by molecular distillation or the like.

As still another known process, there can be mentioned a methyl esterification process comprising saponifying a deodorized distillate, converting the saponified deodorized distillate to a methyl ester and carrying out distillation and concentration as in the ester exchange process. The operation of this process is complicated, and since tocopherols are unstable against alkali, there is a fear of loss of parts of tocopherols during the operation. Furthermore, the same defects as mentioned above with respect to the ester exchange process arise at the steps of distillation and concentration.

Furthermore, there can be mentioned a process in which a deodorized distillate is directly subjected to distillation and fractions are cut to remove free fatty acids. This process, however, is defective in that the viscosity of the distillation residue is high as in the above-mentioned two processes.

SUMMARY OF THE INVENTION

It is a primary object of the present invention to provide a process in which tocopherols can be obtained at a high concentration in a high yield from deodorized distillates by a simple operation with a high efficiency.

In accordance with one aspect of the present invention, there is provided a process for preparing tocopherol concentrates from deodorized distillates formed as by-products at the step of deodorizing oils and fats, which comprises subjecting the deodorized distillate to esterification of free fatty acids by addition of an alcohol or to removal of free fatty acids by distillation and then to hydrogenation and subjecting the hydrogenation product to solvent fractionation to extract tocopherols.

In accordance with another aspect of the present invention, there is provided a process for preparing tocopherol concentrates from deodorized distillates formed as by-products at the step of deodorizing oils and fats, which comprises subjecting the deodorized distillate to esterification of free fatty acids by addition of a polyhydric alcohol having a valency of at least two and then to distillation, and collecting the distillate.

As pointed out hereinbefore, the deodorized distillate that is used in the present invention includes deodorized scums, deodorized sludges and hot well oil dregs formed as by-products at the step of deodorizing oils and fats. Furthermore, tocopherol-containing substances obtained by concentrating these deodorized distillates by distillation such as molecular distillation, steam distillation, reduced pressure distillation or reduced pressure steam distillation, fractionation such as solvent fractionation, or adsorption using silica gel or the like, may be used as the starting substance in the present invention.

DETAILED DESCRIPTION OF THE PREFERRED EMBODIMENTS

As the alcohol that is used for esterification of the deodorized distillate in the process of the first aspect of the present invention, there can be mentioned, for example, monohydric alcohols such as methanol, ethanol and propanol, polyhydric alcohols such as ethylene glycol, propylene glycol, glycerin and erythrite, and dehydration condensates thereof. The esterification is carried out according to customary procedures, and preferably, a solvent such as toluene, xylene or benzene is used for the esterification. The esterification is conducted in the presence or absence of a catalyst such as sulfuric acid, phosphoric acid, p-toluene-sulfonic acid, zinc powder or tin. The esterification temperature is preferably in the range of from 70° to 280° C.

Reduced pressure steam distillation and molecular distillation are especially preferred as distillation for removal of free fatty acids. The reduced pressure steam distillation is carried out at a temperature of 170° to 230° C., preferably 190° to 210° C., under a pressure of less than 25 mmHg, preferably less than 15 mmHg. The molecular distillation is carried out at a temperature of 150° to 250° C., preferably 180° to 240° C., under a pressure of less than 0.01 Torr, preferably less than 0.003 Torr. At the distillation step, parts of tocopherols are distilled, but if the distillation temperature and the degree of reduction of the pressure are adjusted within the above-mentioned ranges, distillation of tocopherols can be controlled to a very low level. It is preferred that the acid value be as low as possible at the point of termination of the distillation, but the acid value is ordinarily adjusted below 5.

A concentration treatment may be carried out after esterification or removal of free fatty acids but before hydrogenation according to need. The above-mentioned distillation, fractionation or adsorption may be adopted for this concentration treatment.

Hydrogenation of the esterified deodorized distillate or the residue left after removal of free fatty acids is accomplished by heating in the presence of a metal catalyst under pressure in a hydrogen atmosphere. As the metal used as the hydrogenation catalyst, there can be mentioned, for example, palladium, platinum, rhodium, ruthenium and nickel, and such metal is ordinarily supported on carbon black, silica or an ion exchange resin. The hydrogenation is carried out at 150° to 250° C. under a hydrogen pressure of 1 to 25 $Kg/cm^2$ according to customary procedures and the hydrogenation is terminated when the iodine value is less than 50, especially less than 45. At the hydrogenation step, hydrocarbons having an unsaturated bonds and triglycerides are hydrogenated, and their melting points are increased and their solubilities at the subsequent solvent fractionation step are reduced. Accordingly, these components are left as solvent-insoluble components at the solvent fractionation step, and tocopherols are effectively extracted into a solvent layer.

The hydrogenation product is then subjected to solvent fractionation. As the solvent used at this step, there can be mentioned, for example, alcohols and hydrous alcohols such as methanol, ethanol, propanol and isopropanol, ketones such as acetone, methylethyl ketone and methylisobutyl ketone, ethers such as dimethyl ether, diethyl ether and dipropyl ether, esters such as methyl acetate and ethyl acetate, and hydrocarbons such as hexane, heptane, petroleum ether and benzene. These solvents may be used singly or in the form of a mixture of two or more of them. It is preferred that the solvent be used in an amount 2 to 50 times (by volume) the amount of the hydrogenation product of the esterified deodorized distillate or the residue left after removal of free fatty acids. The fractionation is carried out at a temperature lower than the boiling point of the solvent and preferably at a temperature lower than 20° C. The temperature need not always be reduced below 0° C. The solvent is added to the hydrogenation product and the mixture is stirred, and the mixture is allowed to stand and the supernatant (solvent layer) is separated. The solvent is removed from the recovered supernatant to obtain a tocopherol concentrate.

The solvent extraction residue contains as main components hydrogenation products of hydrocarbons and triglycerides esters of fatty acids which have been contained in the starting deodorized distillate.

As the polyhydric alcohol having a valency of at least two, that is used for esterification of free fatty acids in the process of the second aspect of the present invention, there can be mentioned, for example, ethylene glycol, polyethylene glycol, propylene glycol, polypropylene glycol, neopentyl glycol, 1,4-butane-diol, 1,3-butylene glycol, 1,6-hexane-diol, 1,5-pentane-diol, glycerin, erythrite, pentaerythrite, trimethylol-ethane, trimethylol-propane, xylose, arabitol, sorbitol, sorbitan, mannitol, mannitan, and dehydration condensates thereof. The polyhydric alcohol is preferably added in an amount about 1.1 times the acid value equivalent of the deodorized distillate.

Esterification is carried out according to customary procedures, and free fatty acids in the deodorized distillate react with a polyhydric alcohol such as mentioned above to form esterification products.

Distillation to be conducted after esterification includes molecular distillation, steam distillation and simple distillation. Distillation may be repeated two times or more. When the steam distillation process is adopted, it sometimes happens that esterification products are decomposed during the distillation and free fatty acids are formed again. In this case, an alcohol is added again to effect esterification and the distillation is then carried out. By the distillation, esterification products of free fatty acids having high boiling points are left in the distillation residue together with triglycerides contained in the deodorized distillate, but the intended tocopherols having lower boiling points are concentrated in the distillate together with hydrocarbons and sterols. The substances other than tocopherols can be separated from the distillate relatively easily by rectification, fractionation or the like.

As is apparent from the foregoing description, the operation efficiency of the process of the present invention is higher than those of the conventional processes and the operation is much easier than in the conventional processes. Furthermore, a product having high quality and high concentration and having a very low impurity content can be obtained according to the present invention. Moreover, in the process of the present invention, since tocopherols are not lost by side reaction or decomposition, the yield of the intended concentrate is high, and the ratio of $\alpha$-, $\beta$-, $\gamma$- and $\delta$-tocopherols in the obtained concentrate is not substantially different from the ratio of tocopherols in the starting deodorized distillate.

The concentration and yield of the product in the process of the second aspect of the present invention are slightly lower than those of the product obtained in the process of the first aspect of the present invention, but the process of the second aspect of the present invention is advantageous over the process of the first aspect of the present invention in that the operation is easier.

The present invention will now be described with reference to the following illustrative Examples that by no means limit the scope of the invention. In these Examples, all of "%" and the quantitative ratios are by weight, and the tocopherol content is one determined according to the Emiry-Engel method.

EXAMPLE 1

A 4-neck flask was charged with 1000 g of a soybean oil deodorized distillate having a tocopherol content of 19.4%, an acid value of 68.8 and an iodine value of 78, and glycerin was added in an amount (41.4 g) 1.1 times the acid value equivalent and esterification was carried out at 240° C. under reflux in xylol. When the acid value was reduced below 0.5, the reaction was stopped and the solvent was removed to obtain 1005 g of an esterification product of the soybean oil deodorized distillate.

To 900 g of the esterification product was added 0.5% (4.5 g) of a hydrogenation nickel catalyst (dispersed in a hardened oil and having a nickel content of 25%), and the mixture was heated at 200° C. under a hydrogen pressure of 2.0 $Kg/cm^2$ for 3 hours to obtain a hydrogenation product having an iodine value of 16. The catalyst was separated by filtration, and the hydrogenation product was divided into parts, each having a weight of 100 g. Then, 300 g of ethanol or hydrous ethanol shown in Table 1 was added to one part (100 g) of the hydrogenation product, the mixture was heated at 45° C. for 10 minutes, cooled to 20° C. and allowed to stand, and the ethanol layer was separated and the solvent was removed therefrom to obtain a tocopherol concentrate shown in Table 1.

TABLE 1

| | Solvent Composition (%) | | |
|---|---|---|---|
| Ethanol | Water | Tocopherol Content (%) | Yield (%) |
| 100 | 0 | 46 | 52 |
| 90 | 10 | 91 | 91 |
| 80 | 20 | 97 | 87 |
| 70 | 30 | 93 | 76 |

EXAMPLE 2

A 4-neck flask was charged with 1000 g of a cotton seed oil deodorized distillate having a tocopherol content of 9.1%, an acid value of 75.4 and an iodine value of 107, and glycerin was added in an amount (45.4 g) 1.1 times the acid value equivalent and esterification was carried out at 180° to 230° C. under reflux in xylol. The reaction was stopped when the acid value was reduced to 0.8, and the solvent was removed. In the same manner as described in Example 1, hydrogenation and extraction with methanol or hydrous methanol were carried out. The obtained results are shown in Table 2.

TABLE 2

| | Solvent Composition (%) | | |
|---|---|---|---|
| Methanol | Water | Tocopherol Content (%) | Yield (%) |
| 100 | 0 | 85 | 53 |
| 98 | 2 | 80 | 65 |
| 95 | 5 | 69 | 55 |

EXAMPLE 3

A 4-neck flask was charged with 1000 g of a linseed oil deodorized distillate having a tocopherol content of 6.8%, an acid value of 70.1 and an iodine value of 87, and pentaerythrite was added in an amount (46.8 g) 1.1 times the acid value equivalent and esterification was carried out at 180° to 240° C. under reflux in xylol. The reaction was stopped when the acid value was reduced to 1.0, and the solvent was removed. In the same manner as described in Example 1, hydrogenation was carried out and the catalyst was removed by filtration. The hydrogenation product was divided into parts, each having a weight of 100 g. A predetermined amount of a solvent shown in Table 3 was added to one part (100 g) of the hydrogenation product, and the mixture was stirred at 45° C. for 10 minutes and allowed to stand still. The solvent layer was separated and the solvent was removed therefrom to obtain a tocopherol concentrate shown in Table 3.

TABLE 3

| Kind of Solvent | Amount of Solvent (ratio to sample) | Tocopherol Content (%) | Yield (%) |
|---|---|---|---|
| methanol | 5 | 82 | 49 |
| isopropanol | 10 | 53 | 41 |
| hexane | 2 | 67 | 58 |

TABLE 3-continued

| Kind of Solvent | Amount of Solvent (ratio to sample) | Tocopherol Content (%) | Yield (%) |
|---|---|---|---|
| acetone | 3 | 71 | 52 |

EXAMPLE 4

To 10 Kg of a soybean oil deodorized distillate having a tocopherol content of 19.4%, an acid value of 68.8 and an iodine value of 78 was added glycerin in an amount (41.4 g) 1.1 times the acid value equivalent, and esterification was carried out at 180° to 240° C. under reflux in xylol. The reaction was stopped when the acid value was reduced below 0.7. The solvent was removed to obtain 10.1 Kg of an esterification product of the soybean oil deodorized distillate.

Then, 10 Kg of the esterification product was subjected to distillation at 180° to 240° C. under 0.002 Torr by a molecular distillation apparatus to obtain 2.5 Kg of a molecular distillation fraction having a tocopherol content of 53.4%.

In the same manner as described in Example 1, 2.0 Kg of the so-obtained fraction was hydrogenated, and 100 g of the hydrogenation product was mixed with 1 Kg of ethanol or hydrous ethanol shown in Table 4 tocopherols were extracted at 25° C. to obtain a tocopherol concentrate shown in Table 4.

TABLE 4

| | Solvent Composition (%) | | |
|---|---|---|---|
| Ethanol | Water | Tocopherol Content (%) | Yield (%) |
| 100 | 0 | 67 | 73 |
| 90 | 10 | 83 | 84 |
| 70 | 30 | 89 | 90 |
| 50 | 50 | 80 | 83 |

EXAMPLE 5

A 4-neck flask was charged with 1000 g of a soybean oil deodorized distillate having a tocopherol content of 17.6%, an acid value of 71.0 and an iodine value of 82, and 4000 g of methanol was added and 2.8 g of p-toluene-sulfonic acid was further added as a catalyst. The mixture was heated and refluxed at 68° to 72° C. to effect esterification. The reaction was stopped when the acid value was reduced to 1.0. The unreacted methanol was removed by distillation, and washing and drying were conducted to obtain 985 g of an esterification product of the soybean oil deodorized distillate.

In the same manner as described in Example 1, 900 g of the esterification product was hydrogenated and divided into parts, each having a weight of 100 g. Then, 300 g of ethanol or hydrous ethanol was added to one part (100 g) of the hydrogenation product and tocopherols were extracted at 25° C. to obtain a tocopherol concentrate shown in Table 5.

TABLE 5

| | Solvent Composition (%) | | |
|---|---|---|---|
| Ethanol | Water | Tocopherol Content (%) | Yield (%) |
| 100 | 0 | 76 | 58 |
| 90 | 10 | 82 | 76 |
| 70 | 30 | 64 | 77 |

EXAMPLE 6

A Claisen flask was charged with 1000 g of a soybean oil deodorized distillate having a tocopherol content of 17.3%, an acid value of 71.0 and an iodine value of 75, and reduced pressure steam distillation was carried out at 200° C. under 7 mmHg. The distillation was stopped when the acid value was reduced to 3.7, and the solvent was removed to obtain 631 g of a fatty acid-removed product of the soybean oil deodorized distillate.

To 600 g of the so-obtained product was 0.5% (3 g) of a hydrogenation nickel catalyst (dispersed in a hardened oil and having a nickel content of 25%), and the mixture was heated at 200° C. under a hydrogen pressure of 2.5 Kg/cm$^2$ for 2 hours to obtain a hydrogenation product having an iodine value of 21. The catalyst was removed by filtration and the hydrogenation product was divided into parts, each having a weight of 100 g. Then, 300 g of ethanol or hydrous ethanol shown in Table 6 was added to one part (100 g) of the hydrogenation product, and the mixture was stirred at 45° C. for 10 minutes, cooled to 20° C. and allowed to stand still. The ethanol layer was separated and the solvent was removed therefrom to obtain a tocopherol concentrate shown in Table 6.

TABLE 6

| Solvent Composition (%) | | Tocopherol Content (%) | Yield (%) |
|---|---|---|---|
| Ethanol | Water | | |
| 100 | 0 | 37 | 85 |
| 90 | 10 | 79 | 82 |
| 80 | 20 | 91 | 75 |
| 70 | 30 | 93 | 72 |

EXAMPLE 7

A Claisen flask was charged with 1000 g of a cotton seed oil deodorized distillate having a tocopherol content of 10.4%, an acid value of 76.0 and an iodine value of 98, and reduced steam distillation was carried out at 195° to 198° C. under 14 mmHg. The distillation was stopped when the acid value was reduced to 1.7. In the same manner as described in Example 6, hydrogenation was carried out and extraction was conducted with methanol or hydrous methanol shown in Table 7 in an amount 5 times the amount of the hydrogenation product. The obtained results are shown in Table 7.

TABLE 7

| Solvent Composition (%) | | Tocopherol Content (%) | Yield (%) |
|---|---|---|---|
| Methanol | Water | | |
| 100 | 0 | 82 | 77 |
| 98 | 2 | 76 | 73 |
| 95 | 5 | 59 | 65 |
| 90 | 10 | 55 | 56 |

EXAMPLE 8

At 200° to 220° C., 20 Kg of a soybean oil deodorized distillate having a tocopherol content of 11.3%, an acid value of 72.0 and an iodine value of 78 was subjected to molecular distillation under 0.01 Torr. In the same manner as described in Example 6, 1.5 Kg of the obtained fraction having a tocopherol content of 33.5% and an acid value of 5.1 was subjected to hydrogenation, and the hydrogenation product was divided into parts, each having a weight of 250 g. Then, 2.5 Kg of ethanol or hydrous ethanol shown in Table 8 was added to one part (250 g) of the hydrogenation product, and tocopherols were extracted at 20° C. to obtain a tocopherol concentrate shown in Table 8.

TABLE 8

| Solvent Composition (%) | | Tocopherol Content (%) | Yield (%) |
|---|---|---|---|
| Ethanol | Water | | |
| 100 | 0 | 78 | 59 |
| 90 | 10 | 88 | 80 |
| 80 | 20 | 82 | 73 |
| 70 | 30 | 68 | 65 |

EXAMPLE 9

At 200° to 205° C., 25 Kg of a soybean oil deodorized distillate having a tocopherol content of 16.8%, an acid value of 70.5 and an iodine value of 76 was subjected to reduced pressure steam distillation under 15 mmHg. The distillation was stopped when the acid value was reduced to 2.0, and 15.8 Kg of a fatty acid-removed product of the soybean oil deodorized distillate.

Then, 15 Kg of the product was subjected to distillation at 180° to 240° C. under 0.002 Torr by a molecular distillation apparatus to obtain 5.3 Kg of a fraction having a tocopherol content of 62.7%.

In the same manner as described in Example 6, 5.0 Kg of the fraction was subjected to hydrogenation, and the hydrogenation product was divided into parts, each having a weight of 1 Kg. Then, 10 Kg of ethanol or hydrous ethanol shown in Table 9 was added, and tocopherols were extracted to obtain a tocopherol concentrate shown in Table 9.

TABLE 9

| Solvent Composition (%) | | Tocopherol Content (%) | Yield (%) |
|---|---|---|---|
| Ethanol | Water | | |
| 100 | 0 | 86 | 65 |
| 90 | 10 | 90 | 89 |
| 80 | 20 | 87 | 81 |
| 70 | 30 | 73 | 75 |

EXAMPLE 10

A Claisen flask was charged with 1000 g of a safflower oil deodorized distillate having a tocopherol content of 5.5%, an acid value of 78.2 and an iodine value of 89, and reduced pressure distillation was carried out at 200° to 205° C. under 6 to 8 mmHg. The distillation was stopped when the acid value was reduced to 0.6. In the same manner as described in Example 6, hydrogenation was carried out until the iodine value was reduced to 10, and the hydrogenation product was divided into parts and extracted with acetone, hexane, petroleum ether or ethyl acetate in an amount 8 times the amount of the hydrogenation product. The obtained results are shown in Table 10.

TABLE 10

| Solvent | Tocopherol Content (%) | Yield (%) |
|---|---|---|
| Acetone | 86 | 73 |
| Hexane | 67 | 82 |
| Petroleum ether | 78 | 71 |
| Ethyl acetate | 69 | 85 |

EXAMPLE 11

A 4-neck flask was charged with 1000 g of a soybean oil deodorized distillate having a tocopherol content of 19.4%, an acid value of 68.8, a saponification value of 133 and an iodine value of 152, and glycerin was added in an amount (41.4 g) 1.1 times the acid value equivalent. Esterification was carried out at 240° C. under reflux in xylol. When the acid value was reduced below 0.5, the reaction was stopped, and the solvent was removed and the obtained esterification product of the soybean oil deodorized distillate was subjected to ordinary steam distillation under 3 Torr to obtain fractions shown in Table 11. It was found that tocopherols were considerably concentrated in the fraction 2.

TABLE 11

| Fraction No. | Distillation Temperature (°C.) | Tocopherol Content (%) | Yield (%) |
| --- | --- | --- | --- |
| 1 | 160–180 | 30.3 | 12.3 |
| 2 | 180–250 | 52.6 | 16.5 |
| 3 | 250–264 | 43.8 | 5.0 |
| 4 | 264–265 | 27.7 | 3.9 |
| residue | | 2.8 | 64.4 |

The fractions 1 through 4 were mixed, and free fatty acids formed during the steam distillation were esterified again with glycerin. The esterification product was subjected to steam distillation again at 170° to 260° C. under 3 Torr to obtain a tocopherol concentrate having a tocopherol content of 56.3% in a yield of 64.8%.

EXAMPLE 12

A glycerin esterification product of a soybean oil deodorized distillate having a tocopherol content of 13.8%, which was prepared in the same manner as described in Example 11, was subjected to molecular distillation at 150° to 220° C. under 0.002 Torr to obtain a concentrate having a tocopherol content of 32.1% in a yield of 32%. The concentrate was subjected to molecular distillation again at 170° to 200° C. under 0.002 Torr to obtain a concentrate having a tocopherol content of 51% in a yield of 46.2%.

EXAMPLE 13

A 4-neck flask was charged with 1000 g of a cotton seed oil deodorized distillate having a tocopherol content of 9.1%, an acid value of 75.4% and a saponification value of 136, and polyethylene glycol (commercially available product having a molecular weight of 1000) was added thereto in an amount (739 g) 1.1 times the acid value equivalent. Esterification was carried out at 180° to 220° C. under reflux in xylol. When the acid value was reduced below 1.0, the reaction was stopped, and the solvent was removed. The esterification product of the cotton seed oil deodorized distillate was subjected to ordinary steam distillation at 200° to 260° C. under 3 Torr to obtain a concentrate having a tocopherol content of 35.8% in a yield of 10.7%.

EXAMPLE 14

A 4-neck flask was charged with 1000 g of a cotton seed oil deodorized distillate having a tocopherol content of 9.1%, an acid value of 75.4 and a saponification value of 136, and trimethylol propane was added in an amount (66.0 g) 1.1 times the acid value equivalent and 0.5% of zinc powder was further added as a catalyst. Esterification was carried out at 165° to 220° C. under reflux in xylol. When the acid value was reduced below 1.0, the reaction was stopped, and the solvent was removed. The esterification product of the cotton seed oil deodorized distillate was subjected to ordinary steam distillation at 200° to 260° C. under 4 Torr to obtain a concentrate having a tocopherol content of 17.8% in a yield of 33.7%.

EXAMPLE 15

A 4-neck flask was charged with 1000 g of a linseed oil deodorized distillate having a tocopherol content of 6.8%, an acid value of 70.1 and a saponification value of 124, and pentaerythrite was added in an amount (46.8 g) 1.1 times the acid value equivalent and 0.5% of zinc powder was further added as a catalyst. Esterification was carried out at 180° to 240° C. under reflux in xylol. When the acid value was reduced below 1.0, the reaction was stopped, and the solvent was removed. Te esterification product of the linseed oil deodorized distillate was subjected to ordinary steam distillation at 200° to 260° C. under 7 Torr to obtain a concentrate having a tocopherol content of 15.6% in a yield of 15.8%.

What is claimed is:

1. A process for preparing tocopherol concentrates from deodorized distillates formed as by-products at the step of deodorizing oils and fats, which comprises subjecting the deodorized distillate to esterification of free fatty acids by addition of a polyhydric alcohol and then to distillation, and collecting the distillate.

2. A process according to claim 1, wherein the polyhydric alcohol is a member selected from the group consisting of ethylene glycol, polyethylene glycol, propylene glycol, polypropylene glycol, neopentyl glycol, 1,4-butane-diol, 1,3-butylene glycol, 1,6-hexane-diol, 1,5-pentane-diol, glycerin, erythrite, pentaerythrite, trimethylol-ethane, trimethylol-propane, xylose, arabitol, sorbitol, sorbitan, mannitol, mannitan and dehydration condensates thereof.

* * * * *